United States Patent
Henry et al.

(10) Patent No.: US 12,084,005 B2
(45) Date of Patent: Sep. 10, 2024

(54) DATA ACQUISITION MODULE FOR AN AGRICULTURAL MACHINE AND RELATED SYSTEMS AND ASSEMBLIES

(71) Applicant: CNH Industrial Canada, Ltd., Saskatoon (CA)

(72) Inventors: James W. Henry, Saskatoon (CA); Joshua Knoblauch, Lowpoint, IL (US); Mark Ridley, Cambridge (GB)

(73) Assignee: CNH Industrial Canada, Ltd. (CA)

(*) Notice: Subject to any disclaimer, the term of this patent is extended or adjusted under 35 U.S.C. 154(b) by 692 days.

(21) Appl. No.: 17/183,561

(22) Filed: Feb. 24, 2021

(65) Prior Publication Data
US 2022/0266801 A1    Aug. 25, 2022

(51) Int. Cl.
*B60S 1/54* (2006.01)
*A01B 79/00* (2006.01)
*G05D 1/00* (2024.01)
*G06V 20/56* (2022.01)

(52) U.S. Cl.
CPC .............. *B60S 1/54* (2013.01); *A01B 79/005* (2013.01); *G05D 1/0094* (2013.01); *G06V 20/56* (2022.01)

(58) Field of Classification Search
CPC .............. A01B 79/005; G05D 1/0094; G05D 2201/0201; G06V 20/56
See application file for complete search history.

(56) References Cited

U.S. PATENT DOCUMENTS

| 2,433,856 A | * | 1/1948 | Marihart | A01B 41/06 250/221 |
| 4,366,878 A | * | 1/1983 | Warf | B60K 13/02 55/385.3 |
| 9,734,400 B2 | | 8/2017 | Shriver | |
| 10,231,376 B1 | | 3/2019 | Stanhope et al. | |
| 10,589,723 B1 | * | 3/2020 | Dubey | G01S 7/497 |

(Continued)

FOREIGN PATENT DOCUMENTS

| DE | 102018203238 | | 9/2019 | |
| EP | 1989936 B1 | * | 10/2012 | ......... A01D 41/1271 |

(Continued)

OTHER PUBLICATIONS

Extended European Search Report for corresponding EP Application No. 22158502 dated Jul. 26, 2022 (10 pages).

(Continued)

*Primary Examiner* — Edelmira Bosques
*Assistant Examiner* — Michael James Giordano
(74) *Attorney, Agent, or Firm* — Rebecca Henkel; Peter Kraft Zacharias; Rickard K. DeMille

(57) ABSTRACT

In one aspect, a system for acquiring data associated with an agricultural field. The system includes an agricultural machine and a data acquisition (DAQ) module supported relative to the agricultural machine. The DAQ module includes a module housing and one or more sensing devices housed within the module housing. The one or more sensing device are configured to generate data associated with a condition of a field as the agricultural machine travels across the field. In addition, the system includes an air circulation system provided in operative association with the DAQ module that is configured to direct an airflow into an interior of the module housing for circulation therein.

15 Claims, 6 Drawing Sheets

(56) References Cited

U.S. PATENT DOCUMENTS

| | | | |
|---|---|---|---|
| 10,916,028 | B1 | 2/2021 | Barrick |
| 2012/0091123 | A1* | 4/2012 | Joines |
| 2018/0015907 | A1* | 1/2018 | Rice ........................ B60S 1/56 |
| 2018/0210450 | A1 | 7/2018 | Ferrari et al. |
| 2019/0104722 | A1 | 4/2019 | Slaughter et al. |
| 2019/0150357 | A1 | 5/2019 | Wu et al. |
| 2019/0236359 | A1 | 8/2019 | Posselius |
| 2019/0294914 | A1 | 9/2019 | Fevold et al. |
| 2019/0377986 | A1 | 12/2019 | Ferarri et al. |
| 2019/0392263 | A1 | 12/2019 | Ferarri et al. |
| 2020/0029490 | A1 | 1/2020 | Bertucci et al. |
| 2020/0084963 | A1* | 3/2020 | Gururajan ............ A01D 43/087 |
| 2020/0149933 | A1* | 5/2020 | Robertson, Jr. ...... G01D 11/245 |
| 2021/0181078 | A1* | 6/2021 | Marzu ................... G06T 7/0012 |
| 2022/0150392 | A1 | 5/2022 | Maddox et al. |

FOREIGN PATENT DOCUMENTS

| | | | |
|---|---|---|---|
| EP | 3875691 | A1 | 9/2021 |
| KR | 20010084756 | A | 9/2001 |
| WO | WO 2019040866 | | 2/2019 |
| WO | WO 2019137843 | | 7/2019 |
| WO | WO2019197741 | A1 | 10/2019 |

OTHER PUBLICATIONS

Vázquez-Arellano, "3-D Imaging Systems for Agricultural Applications—A Review", Sensors, dated Apr. 29, 2016 (24 pages) https://www.mdpi.com/1424-8220/16/5/618.

* cited by examiner

DATA ACQUISITION MODULE FOR AN AGRICULTURAL MACHINE AND RELATED SYSTEMS AND ASSEMBLIES

FIELD OF THE INVENTION

The present subject matter relates generally to the agricultural machines and, more particularly, to a data acquisition module for an agricultural machine that can be used to acquire data associated with one or more conditions of an agricultural field, as well as related systems and/or assemblies incorporating and/or configured for use with the data acquisition module.

BACKGROUND OF THE INVENTION

Various sensor-based systems have been developed for use with an agricultural machine to detect or monitor one or more conditions associated with an agricultural field, such as one or more surface conditions (e.g., residue coverage) and/or sub-surface conditions (e.g., soil compaction). However, these conventional systems typically suffers from one or more drawbacks. For instance, given that agricultural machines often operate in dirty/dusty environments, obtaining reliable, accurate sensor data is often difficult, particularly when cameras or other imaging devices are being used to acquire images of the field. In this regard, dirt and dust can not only soil the exposed optical surfaces of the imaging devices, but can also flow through the field of view of the imaging devices, thereby resulting in images being captured that are difficult to process using computer-vision techniques. Moreover, as conventional sensor-based systems increase in complexity (including the amount of componentry associated therewith) and/or are adapted to function in various operating conditions (e.g., low-light conditions, such as nighttime conditions), the amount of heat generated by the various system components can often be problematic, leading to overheating and/or component failure.

Accordingly, a data acquisition module for an agricultural machine and/or related systems/assemblies incorporating and/or configured for use with the data acquisition module that address one or more issues associated with conventional sensor-based systems adapted to obtain data associated with an agricultural field would be welcomed in the technology.

BRIEF DESCRIPTION OF THE INVENTION

Aspects and advantages of the invention will be set forth in part in the following description, or may be obvious from the description, or may be learned through practice of the invention.

In one aspect, the present subject matter is directed to a system for acquiring data associated with an agricultural field. The system includes an agricultural machine and a data acquisition (DAQ) module supported relative to the agricultural machine. The DAQ module includes a module housing and one or more sensing devices housed within the module housing. The one or more sensing device are configured to generate data associated with a condition of a field as the agricultural machine travels across the field. In addition, the system includes an air circulation system provided in operative association with the DAQ module that is configured to direct an airflow into an interior of the module housing for circulation therein.

In another aspect, the present subject matter is directed to a system for acquiring data associated with an agricultural field. The system includes an agricultural machine and a data acquisition (DAQ) module supported relative to the agricultural machine. The DAQ module includes a module housing, an optical window forming a portion of a bottom wall of the module housing, and one or more imaging devices configured to capture images of a portion of the field as the agricultural machine travels across the field. The one or more imaging devices are positioned within the module housing relative to the optical window such that a field of view of the one or more imaging devices is directed through the optical window. Additionally, the system includes a drape assembly suspended relative to the one or more imaging devices. The drape assembly is configured to at least partially shroud an imaging volume located underneath the DAQ module that encompasses the field of view of the one or more imaging devices.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
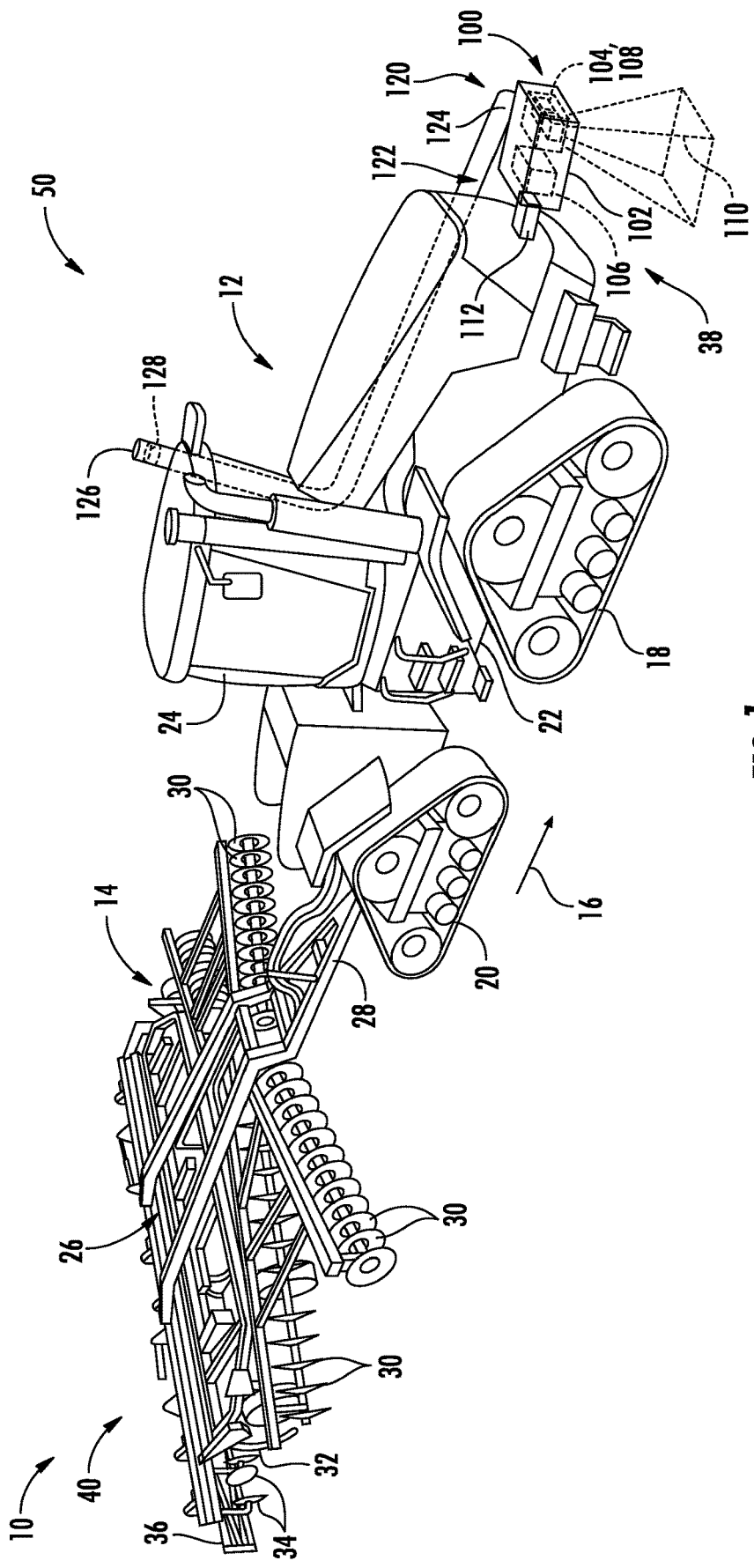
FIG. 1 illustrates a perspective view of one embodiment of a system for acquiring data associated with an agricultural field in accordance with aspects of the present subject matter, particularly illustrating the system include an agricultural machine and a data acquisition module for acquiring data associated with the field across which the machine is being traversed.

Reference now will be made in detail to embodiments of the invention, one or more examples of which are illustrated in the drawings. Each example is provided by way of explanation of the invention, not limitation of the invention.

In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to a data acquisition (DAQ) module for an agricultural machine that can be used to acquire data associated with one or more conditions of an agricultural field. In several embodiments, the DAQ module may include one or more sensing devices for collecting or generating data associated with one or more conditions of a field. For instance, the DAQ module may include one or more imaging devices for capturing images of a field as the associated agricultural machine travel across the field. Such images may, for example, allow one or more surface conditions of the field to be detected or monitored, such as one or more conditions or parameters associated with crop residue, soil clods, surface levelness or irregularities (e.g., ridges and/or valleys), and/or the like within the field.

Additionally, in accordance with aspects of the present subject matter, the DAQ module may be operatively associated with an air circulation system for providing a supply of air within the interior of the DAQ module for circulation therein. As will be described below, the air circulated within the interior of the module housing may serve a dual-purpose, namely to provide an airflow for: (1) cooling any heat-generating components of the DAQ module; and (2) cleaning one or more optical components of the DAQ module (e.g., an optical window through which the imaging device(s) is configured to capture images of the field).

Moreover, in several embodiments, a drape assembly may be configured to be supported relative to the DAQ module. The drape assembly may generally be configured to at least partially shroud an "imaging volume" located directly below the DAQ module that encompasses the field of view of the imaging device(s) of the DAQ module. As a result, the drape assembly may function to prevent or minimize the amount of dust or debris that is directed across or through the field of view of the imaging device(s).

Referring now to drawings, FIG. 1 illustrates a perspective view of one embodiment of a system 50 for acquiring data associated with an agricultural field in accordance with aspects of the present subject matter. In general, the system 50 includes an agricultural machine 10 and a data acquisition module 100 provided in association with the agricultural machine for acquiring data associated with a field as the machine 10 travels across the field.

In the illustrated embodiment, the agricultural machine 10 includes a work vehicle 12 and an associated agricultural implement 14. In general, the work vehicle 12 is configured to tow the implement 14 across a field in a direction of travel (e.g., as indicated by arrow 16 in FIG. 1). As shown in FIG. 1, the work vehicle 12 is configured as an agricultural tractor and the implement 14 is configured as an associated tillage implement. However, in other embodiments, the work vehicle 12 may be configured as any other suitable type of vehicle, such as an agricultural harvester, a self-propelled sprayer, and/or the like. Similarly, the implement 14 may be configured as any other suitable type of implement, such as a planter. Furthermore, it should be appreciated that the agricultural machine 10 may correspond to any suitable powered and/or unpowered agricultural machine (including suitable vehicles and/or equipment, such as only a work vehicle or only an implement). Additionally, the agricultural machine 10 may include more than two associated vehicles, implements, and/or the like (e.g., a tractor, a planter, and an associated air cart).

As shown in FIG. 1, the work vehicle 12 includes a pair of front track assemblies 18, a pair or rear track assemblies 20, and a frame or chassis 22 coupled to and supported by the track assemblies 18, 20. An operator's cab 24 may be supported by a portion of the chassis 22 and may house various input devices for permitting an operator to control the operation of one or more components of the work vehicle 12 and/or one or more components of the implement 14. Additionally, as is generally understood, the work vehicle 12 may include an engine (not shown) and a transmission (not shown) mounted on the chassis 22. The transmission may be operably coupled to the engine and may provide variably adjusted gear ratios for transferring engine power to the track assemblies 18, 20 via a drive axle assembly (not shown) (or via axles if multiple drive axles are employed).

Additionally, as shown in FIG. 1, the implement 14 may generally include a carriage frame assembly 26 configured to be towed by the work vehicle 12 via a pull hitch or tow bar 28 in the direction of travel 16 of the vehicle 12. As is generally understood, the carriage frame assembly 26 may be configured to support a plurality of ground-engaging tools, such as a plurality of shanks, disk blades, leveling blades, basket assemblies, tines, spikes, and/or the like. For example, in the illustrated embodiment, the carriage frame assembly 26 is configured to support various gangs of disc blades 30, a plurality of shanks 32, a plurality of leveling blades 34, and a plurality of crumbler wheels or basket assemblies 36. However, in alternative embodiments, the carriage frame assembly 26 may be configured to support any other suitable ground engaging tools and/or combination of ground engaging tools. In several embodiments, the various ground-engaging tools may be configured to perform a tillage operation or any other suitable ground-engaging operation across the field along which the implement 14 is being towed. It should be understood that, in addition to being towed by the work vehicle 12, the implement 14 may also be a semi-mounted implement connected to the work vehicle 12 via a two point hitch (not shown) or the implement 14 may be a fully mounted implement (e.g., mounted the work vehicle's 12 three point hitch (not shown)).

It should also be appreciated that the configuration of the agricultural machine 10 described above and shown in FIG. 1 is provided only to place the present subject matter in an exemplary field of use. Thus, it should be appreciated that the present subject matter may be readily adaptable to any manner of machine configuration, including any suitable work vehicle configuration and/or implement configuration. For example, in an alternative embodiment of the work vehicle 12, a separate frame or chassis may be provided to which the engine, transmission, and drive axle assembly are coupled, a configuration common in smaller tractors. Still other configurations may use an articulated chassis to steer the work vehicle 10, or rely on tires/wheels in lieu of the track assemblies 14, 16. Similarly, as indicated above, the carriage frame assembly 26 of the implement 12 may be configured to support any other suitable combination of type of ground-engaging tools.

Furthermore, as indicated above, the disclosed system 50 may also include a data acquisition (DAQ) module 100 configured to be installed relative to or otherwise associated with the agricultural machine 10. For instance, in the illustrated embodiment, the DAQ module 100 is installed relative to the work vehicle 12, such as by being mounted at a forward end 38 of the work vehicle 12. However, in other embodiments, the DAQ module 100 may be installed relative to the implement 14, such as by being mounted at an aft end 40 of the implement 14.

In general, the DAQ module 100 may include an outer module housing 102 configured to encase or enclose a plurality of DAQ-related components. For instance, in several embodiments, the DAQ module 100 may include one or more sensing devices 104 supported within the module housing 102 for acquiring data associated with the field across which the agricultural machine 10 is being traversed. In addition, the DAQ module 100 may include one or more additional components 106 housed within the module housing 102. For instance, such additional components 106 may include, but are not limited to, one or more CPUs or controllers, lighting devices, light source drives, sensors, heat dissipation components, power sources, power converters, and/or the like, examples of some which will be described below with reference to FIGS. 2 and 3.

In accordance with aspects of the present subject matter, the sensing devices 104 of the DAQ module 100 may include one or more imaging devices 108 configured to capture images or other image data relating to one or more surface conditions of the field. Suitable surface conditions may include, but are not limited to, conditions or parameters associated with crop residue, soil clods, surface levelness or irregularities (e.g., ridges and/or valleys), and/or the like within the field.

In several embodiments, the imaging device(s) 108 may be supported relative to the agricultural machine 10 such that the imaging device(s) 108 has a field of view 110 directed towards a portion(s) of the field adjacent to the work vehicle 12 and/or the implement 14, such as a portion(s) of the field disposed in front of, behind, and/or along one or both of the sides of the work vehicle 12 and/or the implement 14. For example, in the embodiment shown in FIG. 1 in which the DAQ module 100 is mounted at the forward end 38 of the work vehicle 12, the imaging device(s) 108 has a field of view 110 directed towards a section of the field disposed in front of the work vehicle 12. Such a forward-located imaging device(s) 108 may allow pre-operation images of the field to be captured for monitoring or determining surface conditions of the field prior to the performance of an agricultural operation (e.g., a tillage operation). Alternatively, in an embodiment in which the DAQ module 100 is mounted at the aft end 40 of the implement 14, the imaging device(s) 108 may, for example, have a field of view directed towards a section of the field disposed behind the implement 14. Such an aft-located imaging device(s) 108 may allow post-operation images of the field to be captured for monitoring or determining surface conditions of the field after the performance of an agricultural operation (e.g., a tillage operation).

In general, the imaging device(s) 108 may correspond to any suitable device(s) or other assembly configured to capture images of the field. For instance, in several embodiments, the imaging device(s) 108 may correspond to a stereo camera assembly having first and second cameras incorporated therein or otherwise forming a part thereof. In such embodiments, the stereo camera assembly may be used to capture/generate both two-dimensional and three-dimensional images of the field. Specifically, each camera may include a lens and a separate image sensor for capturing two-dimensional images. Additionally, by simultaneously capturing an image of the same portion of the field with each camera, the separate images can be combined, compared and/or otherwise processed to extract three-dimensional information about such portion of the field. For example, by comparing the images captured by each camera, a depth image can be generated that allows the scene depth to be determined (e.g., relative to the camera) at each corresponding pixel location within the imaged portion of the field, which, in turn, can be converted into a scene height (or pixel height) at each corresponding pixel location relative to a reference plane (e.g., a reference plane approximating the soil surface). As a result, the relative height of specific features or points within the field may be determined, such as the relative height of residue or soil clods within the field.

It should be appreciated that, in addition to a stereo camera assembly or as an alternative thereto, the DAQ module 100 may include any other suitable type of imaging device(s) 108. For instance, suitable imaging devices 108 may also include single or non-stereo cameras, stereoscope cameras, multi-spectrum cameras and/or the like. It should also be appreciated that, in addition to one or more imaging device(s) 108 (or as an alternative thereto), the DAQ module 100 may include any other suitable sensing device(s) 104 associated with monitoring one or more conditions of the field, such as a radar sensor, ultrasound sensor, and/or the like. For instance, in one embodiment, the sensing device(s) may include a ground-penetrating radar(s) for monitoring one or more sub-surface conditions associated with the field (e.g., soil compaction).

It should also be appreciated that the DAQ module 100 may be configured to be mounted or otherwise supported relative to a portion of the agricultural machine 10 using any suitable mounting/support structure. For instance, as shown in FIG. 1, the DAQ module 100 may be mounted to the front of the work vehicle 12 via suitable mounting structure 112 (e.g., a frame, mounting arms, brackets, trays, etc.). Such mounting structure 112 may, for example, permit the imaging device(s) 108 to be supported out in front of the vehicle 12 (e.g., in a cantilevered arrangement) in a manner that allows the imaging device(s) 108 to obtain the desired field of view 110, including the desired orientation of the device's field of view 110 relative to the surface of the field (e.g., a straight-down view oriented generally perpendicular to the surface of the field).

Additionally, in several embodiments, the disclosed system 50 may also include an air circulation system 120 for providing a supply of air within the interior of the module housing 102 for circulation therein. As will be described below, the air circulated within the interior of the module housing 102 via operation the air circulation system 120 may serve a dual-purpose, namely to provide an airflow for: (1) cooling any heat-generating components of the DAQ module 100; and (2) cleaning one or more optical components of the DAQ module 100 (e.g., an optical window through which the imaging device(s) 108 is configured to capture images of the field).

As shown in FIG. 1, the air circulation system 120 may include an air intake conduit 122 fluidly coupled to the module housing 102 (e.g., via an air intake port defined through the housing 102) to allow air to be suppled into the housing 102 via the conduit 122. In several embodiments, the intake conduit 122 may extend lengthwise between an output end 124 coupled to the module housing 102 and an intake end 126 spaced apart from the module housing 102, with the intake conduit 122 being configured to intake air at its intake end 126 and expel such air into the module housing 102 at its output end 124. In this regard, the length of and/or mounting arrangement for the intake conduit 122 may be selected, for instance, to allow the intake end 126 of the conduit 122 to be positioned at a suitable location for intaking relatively clean air. For example, as shown in FIG. 1, the air intake conduit 122 is coupled to and routed along an exterior of the work vehicle 12 such that the intake end 126 of the conduit 122 is positioned at a location proximal to the operator's cab 24 (e.g., at or adjacent to the roof of the cab 24), thereby allowing the conduit 122 to intake substantially dust-free air for delivery into the DAQ module 100. Additionally, in several embodiments, a filter 128 may also be provided in association with the air intake conduit 122 (e.g., at the intake end 126 of the conduit 122) for filtering out dust or other particulates within the air. In one embodiment, the filter 128 may correspond to a reusable filter that can be periodically washed or otherwise cleaned and then reinstalled relative to the intake conduit 122.

Figure 2:
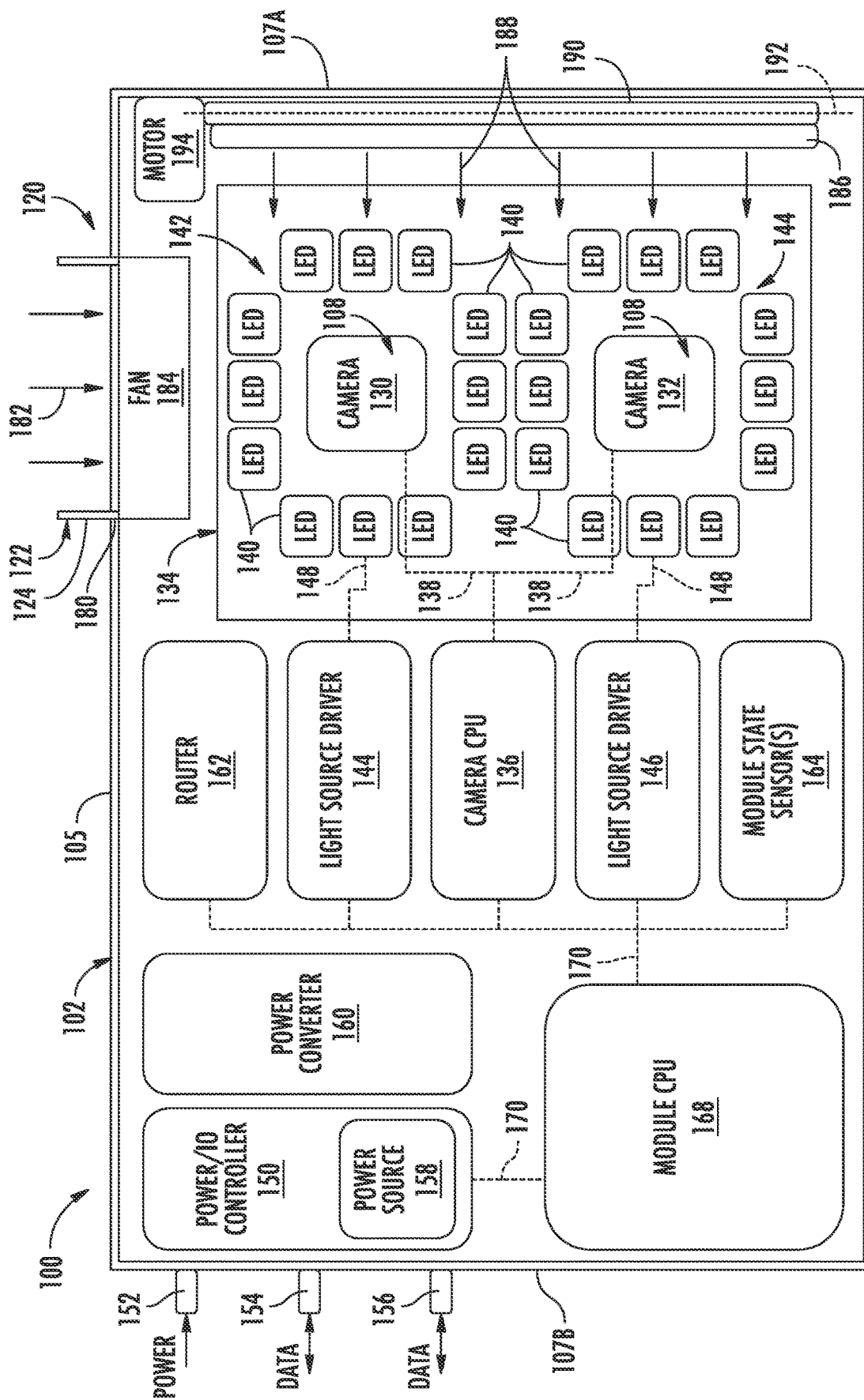
FIG. 2 illustrates a schematic view of one embodiment of a DAQ module suitable for use within one or more embodiments of a system for acquiring data associated with an agricultural field in accordance with aspects of the present subject matter.

Referring now to FIG. 2, a schematic view of one embodiment of a DAQ module 100 suitable for use within one or more embodiments of a system for acquiring data associated with an agricultural field is illustrated in accordance with aspects of the present subject matter. For purposes of discussion, the DAQ module 100 shown in FIG. 2 will generally be described with reference to the agricultural machine 10 and related system 50 described above with reference to FIG. 1. However, it should be appreciated that the DAQ module 100 may, in general, be configured for use with any suitable agricultural machine having any suitable machine configuration and/or within a system having any other suitable system configuration.

As indicated above, the DAQ module 100 includes a module housing 102 configured to encase or enclose a plurality of DAQ-related components. For instance, one or more imaging device(s) 108 may be disposed within the module housing 102 for capturing images of the portion of the field located adjacent to the DAQ module 100 (e.g., immediately below the DAQ module 100). As shown in FIG. 2, the imaging device(s) 108 may, in several embodiments, correspond to a stereo camera assembly having first and second cameras 130, 132 spaced apart from one another within the module housing 102 for capturing or generating both two-dimensional and three-dimensional images of the field. In one embodiment, the first and second cameras 130, 132 may be mounted or supported within the module housing 102 relative to an optical window (e.g., as indicated by rectangle 134 shown in FIG. 2) through which the cameras 130, 132 are configured to capture images. For instance, the optical window 134 (e.g., a glass or transparent polymer-based window) may be configured to form all or a portion of a bottom wall 103 (FIG. 3) of the module housing 102. As such, with the cameras 130, 132 supported within the module housing 102 directly above the optical window 134, the field of view 110 (FIG. 1) of each camera 130, 132 may be directed through the window 134 to allow images of the underlying field to be captured. In one embodiment, the cameras 130, 132 may be positioned within a forward portion of the module housing 102, such as at a location closer to a front wall 107A of the module housing 102 than an opposed rear wall 107B of the module housing. Such positioning may, for example, allow the rear portion of the module housing 102 to be mounted to an associated supported structure or frame assembly (e.g., as will be described below with reference to FIGS. 4 and 5) while providing the cameras 130, 132 with an unobstructed view of the underlying portion of the field.

Additionally, it should be appreciated that, in several embodiments, the operation of the cameras 130, 132 may be controlled based on the ground speed of the associated agricultural machine 10. Specifically, in one embodiment, the image capture timing for the cameras 130, 132 may be speed-dependent such that the frequency at which the cameras 130, 132 capture images of the field is varied based on the ground speed of the associated agricultural machine 10. Such speed-dependent image capture timing may, for instance, allow for the field to be imaged with minimal/no gaps or overlap between consecutive images.

As shown in FIG. 2, the DAQ module 100 may also include a camera controller or central processing unit (CPU) 136 communicatively coupled to each camera 130, 132 (e.g., via communication link(s) 138). In one embodiment, the camera CPU 136 may be configured to control the operation of each camera 130, 132, such as by controlling the timing and/or rate at which each camera 130, 132 captures images of the field. For instance, the camera CPU 136 may be configured to trigger each camera 130, 132 to simultaneously capture an image of an underlying portion of the field, thereby allowing images of the same portion of the field to be captured from each camera's perspective. Additionally, in one embodiment, the camera CPU 136 may be configured to receive the individual images captured by each camera 130, 132 and execute a suitable image processing algorithm(s) (e.g., software-based and/or hardware-based image processing) to generate a disparity map or depth image associated with the imaged portion of the field. The original image received from each camera 130, 132 and/or the depth image deriving therefrom may then be stored in memory associated with the camera CPU 136 and/or transmitted to a separate computing device or controller (e.g., a separate module CPU 168 of the DAQ module 100, as will be described below) for storage and/or subsequent processing/analysis.

Additionally, the DAQ module 100 may also include one or more lighting devices configured to provide a source of artificial lighting used to illuminate the portion of the field being imaged by the cameras 130, 132. For instance, as shown in FIG. 2, the DAQ module 100 includes a plurality of lighting devices 140 installed relative to the cameras 130, 132, such as a first array 142 of lighting devices 140 installed around the first camera 130 and a second array 144 of lighting devices 140 installed around the second camera 132. In such an embodiment, each lighting device 140 may be installed within the footprint of or may otherwise aligned with the optical window 134 provided in association with the module housing 102 so that light from each lighting device 140 can be transmitted through the window 134 for illuminating the underlying portion of the field. For instance, in one embodiment, the various lighting devices 140 may be supported within the module housing 102 directly above the optical window 134 (e.g., similar to the cameras 130, 132). Additionally, in one embodiment, the lighting devices 140 may be configured to be strobed or otherwise activated or turned on for a very short time period corresponding to the image acquisition period of the cameras 130, 132. Such strobing of the lighting devices 140 minimizes power consumption and also reduces the amount of heat generation.

In several embodiments, the lighting devices 140 may correspond to light-emitting diodes (LEDs), such as high intensity/power LEDs. Such high intensity/power LEDs may be particularly advantageous for use in low-lighting conditions, such as during nighttime operation of the agricultural machine 10 or during other low-light conditions, to improve the overall performance of the DAQ module 100 (particularly the performance of the cameras 130, 132). However, it should be appreciated that, in other embodiments, each lighting device 140 may correspond to any other suitable artificial light source(s).

As shown in FIG. 2, the DAQ Module 100 may also include one or more light source drivers 144, 146 electrically coupled to the lighting devices 140 (e.g., via links 148) for regulating the power supplied to each lighting device 140. Specifically, in the illustrated embodiment, a first light source driver 146 is provided to regulate the power supply to the first array 142 of lighting devices 140 and a second light source driver 148 is provided to regulate the power supply to the second array 144 of lighting devices 140. It should be appreciated that, in embodiments in which the lighting devices 140 comprise LEDs, the light source drivers 144, 146 may correspond to LED drivers. Additionally, a related capacitor (e.g., an LED drive capacitor) may also be included within the DAQ module 100 for smoothing the voltage being supplied to each light source driver 144, 146 from an associated power supply. The capacitor may also be used as a local power store to provide a short, high current burst when the lighting devices 140 are activated during image acquisition via the cameras 130, 132.

Referring still to FIG. 2, the DAQ module 100 may also include a power and input-output (IO) controller 150 (hereinafter power/IO controller 150) for regulating the power supplied to the various components housed within the DAQ module 100 and/or for providing a gateway for data and other inputs/outputs being received by and/or transmitted from the DAQ module 100. For instance, the power/IO controller 150 may be electrically coupled to a power input socket 152 through which power (e.g., a 12 volt power supply) is supplied to the DAQ module 100 from an external source, such as the agricultural machine 10 (e.g., the work vehicle 12). Additionally, the power/IO controller 150 may be communicatively coupled to various data ports for receiving/transmitting data and related communications from/to the agricultural machine 10 (e.g., the work vehicle 12), such as one or more first data ports 154 for receiving/transmitting ISOBUS data/communications, CANBUS data/communications, and/or any other data/communications transmitted according to any suitable protocol and one or more second data ports 156 for receiving/transmitting additional data/information.

As shown in FIG. 2, in addition to being coupled to an external power source (e.g., the agricultural machine 10 via the power input socket 152), the DAQ module 100 may optionally include an onboard power source 158, such as an onboard battery. In one embodiment, the onboard power source 158 may serve as a back-up power source for the DAQ module 100, but, in other embodiments, may function as the primary power source for one or more components of the DAQ module 100. Moreover, as shown in FIG. 2, the DAQ module 100 may also include a power converter 160 for adjusting the voltage or current of the power being supplied to the various components of the DAQ module 100 and/or for transforming the power input to a different form (e.g., AC-to-DC conversion or DC-to-AC conversion).

Moreover, as shown in FIG. 2, the DAQ module 100 may also include an onboard router 162 for providing wireless communications between the DAQ module 100 and/or one or more separate devices, such as one or more separate CPUs, computing devices and/or the like. For instance, in one embodiment, the router 162 may be used to wirelessly transmit data acquired or generated by the DAQ module 100 to a user interface associated with the agricultural machine 10 (e.g., a display panel or other user interface housed within the cab 24 of the work vehicle 12) or any other remote computing device, such as client device of the operator of the agricultural machine 10 (e.g., a smartphone or tablet) or a remote server. The router 162 may also provide a back-up data connection to the agricultural machine 10 in the event that the wired data connection (e.g., via the data ports 154, 156) is lost.

Referring still to FIG. 2, the DAQ module 100 may also include one or more module state sensors 164 for monitoring one or more operating conditions or states of the DAQ module 100. For instance, in one embodiment, the module state sensor(s) 164 may correspond to one or more accelerometers, gyroscopes, inertial measurement units (IMUs) and/or the like for monitoring the orientation (e.g., tilting of the DAQ module 100 relative to a two-dimensional plane) and/or vibrational movement of the DAQ module 100. In one embodiment, the monitored orientation may, for example, be used to correct or adjust one or more portions of the data being acquired and/or generated by the DAQ module 100, such as the depth images being generated based on the two-dimensional images captured by the cameras 130, 132. In another embodiment, the module state sensor(s) 164 may correspond to one or more temperature sensors configured to monitor the temperature within the module housing 102. As will be described below, such temperature measurements may, for example, be used to control one or more components of the air circulation system 120.

Additionally, the DAQ module 100 may also include a module controller or CPU 168 for controlling the operation of one or more components of the DAQ module 100 and/or for storing/processing data acquired or generated by one or more of the DAQ-related components. For instance, as shown in FIG. 2, the module CPU 168 may be communicatively coupled (e.g., via links 170) to various different components of the DAQ module 100 (e.g., the camera CPU 136, light source drivers, 144, 146, router 162, module state sensor(s) 164, power/IO controller 150, and/or the like) for allowing data, control commands, and/or other signals to be transmitted between such components. For instance, images received at or generated by the camera CPU 136 and/or sensor data generated by the module state sensor(s) 164 may be transmitted to the module CPU 168 for storage thereon and/or for subsequent processing and/or analysis. Similarly, data stored at and/or generated by the module CPU 168 (e.g., image data and/or surface condition data) may be transmitted from the module CPU 168 to the power/IO controller 150 for subsequent transmission to the agricultural machine 10 (e.g., via the data port(s) 154, 156) and/or to the router 164 for subsequent wireless transmission to a separate device (e.g., a client device or any other suitable wireless-enabled device).

In several embodiments, the module CPU 168 may also be configured to execute one or more image processing algorithms for analyzing the images received from the camera CPU 136 (e.g., the original 2-D images captured by the cameras 130, 132 and/or the depth images generated by the camera CPU 136) to identify one or more surface conditions associated with the imaged portion of the field. For instance, the two-dimensional images may be analyzed to differentiate crop residue from soil within the imaged portion of the field (e.g., using a texture-based, color-based, and/or spectral-based analysis), thereby allowing the percent crop residue coverage within the field to be approximated. Similarly, the 3-D or depth images can be analyzed to identify the presence of soil clods within the imaged portion of the field, as well as to approximate the size of such clods. In addition, the depth images can be analyzed to identify the height/depth of any ridges/valleys within the field and/or the heights associated with any residue bunches within the field.

Referring still to FIG. 2, as indicated above, the DAQ module 100 may also be provided in operative association with an air circulation system 120 configured to circulate an airflow through the module housing 102 to provide cooling for any heat-generating components of the DAQ module 100 (e.g., lighting devices 140, cameras 130, 132, CPUs, controllers, and/or the like) and to clean-off one or more optical components of the DAQ module 100 (e.g., the optical window 134). As indicated above, the air circulation system 120 may include an intake conduit 122 (a portion of which is shown in FIG. 2) for supplying an airflow into the module housing 102. Additionally, as shown in FIG. 2, the output end 124 of the intake conduit 122 is fluidly coupled to an intake port 180 defined through a sidewall 105 of the module housing 102 to allow the airflow (indicated by arrows 182) directed through the intake conduit 122 to be suppled into the interior of the module housing 102.

Moreover, as shown in FIG. 2, the air circulation system 120 may also include a fan 184 provided in fluid communication with the intake port 180 and the output end 124 of the intake conduit 122. In general, the fan 184 may be configured to generate a suction force or vacuum within the intake conduit 122 that draws air in through the intake end 126 (FIG. 1) of the conduit 122 for delivery through the conduit 122 to the module housing 102. In one embodiment, the fan 184 may be configured generate a sufficient airflow through the conduit 122 and into the module housing 102 in order to pressurize the housing 102 to a positive pressure (i.e., above the ambient pressure outside the housing 102), thereby preventing the entry of dust or other particulates into the housing 102 via any openings or other entryways defined therein.

By providing a pressurized airflow into the module housing 102, the air may be circulated throughout the housing 102 to cool any heat-generating components of the DAQ module 100. For instance, the airflow through the housing 102 may serve as a cooling airflow for the lighting devices 140, the cameras 130, 132, the various CPUs and controllers, the power converter 160, and/or any other suitable heat-generating components encased within the module housing 102. Such cooling may be particularly beneficial when the lighting devices 140 correspond to high power/intensity LEDs, as such components are typically sources of a substantial amount of heat generation.

It should be appreciated that, in embodiments in which the airflow provided within the module housing 102 is used to cool the heat-generating components of the DAQ module 100, the operation of the fan 184 may, for example, be controlled based on a sensed or monitored temperature within the module housing 102. For instance, when the module state sensor(s) 164 comprises one or more temperature sensors, the module CPU 168 or any other suitable CPU or controller may be configured to monitor the temperature within the module housing 102 via the feedback provided by sensor(s). The operation of the fan 184 may then be controlled, for example, to activate or turn on the fan 184 when the monitored temperature exceeds a predetermined threshold.

Additionally, the pressurized airflow provided within the module housing 102 may also provide a means for cleaning off one or more contaminated surfaces of the optical components of the DAQ module 100, such as the optical window 134. For instance, in one embodiment, an air labyrinth or knife 186 may be provided at or adjacent to the optical window 134 that is configured to direct a knife or jet of pressurized air (indicated by arrows 188) across an external surface 135 (FIG. 3) of the optical window 134 to clean such external surface.

Moreover, in several embodiments, the air circulation system 140 may also include an air flap 190 provided in operative association with the air knife 186 to allow an opening or flow channel 187 (FIG. 3) of the air knife 186 to be opened/closed or sealed/unsealed) to allow the pressurized air within the interior of the module housing 102 to be selectively diverted through the air knife 186. In one embodiment, the air flap 190 may be rotatable or pivotable (e.g., about a pivot axis 192) between an opened position, at which the air within the interior of the module housing 102 can be expelled through the flow channel 187 of the air knife 186, and a closed position, at which the flap 190 seals or otherwise covers the flow channel 187 prevents the passage of air or dust therethrough). In such an embodiment, a suitable drive device, such as a motor 194 (e.g., a servomotor), may be provided in operative association with the air flap 190 to actuate the flap 190 between the opened and closed positions.

In one embodiment, the operational state of the air flap 190 (e.g., opened or closed) may be varied as a function of the operational state of the fan 184 (e.g., on or off). Specifically, when the fan 184 is deactivated or otherwise turned off, the air flap 190 may be moved to the closed position (e.g., via operation of the motor 194) to seal the associated flow channel 187 of the air knife 186 and, thus, prevent dust, particulates, and/or other contaminates from entering the housing 102. In contrast, when the fan is activated and generating a positive air pressure within the module housing 102, the air flap 190 may be moved to the opened position (e.g., via operation of the motor 194) to allow the pressurized air to be directed through the air knife 186 to facilitate cleaning of the optical window 145. In such instance, given the positive pressure within the module housing 102, contaminates outside the module housing 102 will be prevented from entering the housing 102 due to the air stream being expelled through the flow channel 187 of the air knife 186.

Figure 3:
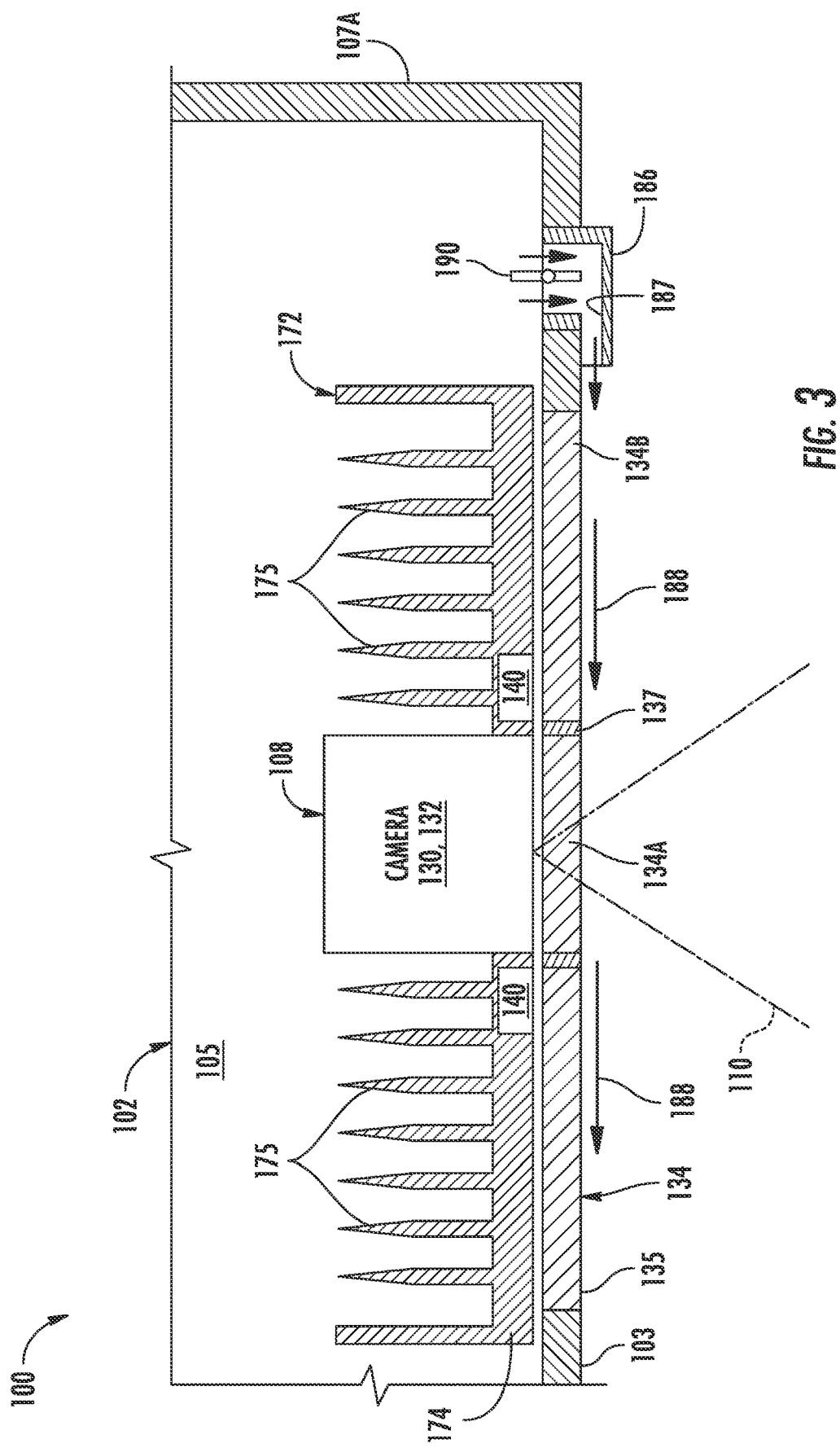
FIG. 3 illustrates a simplified, schematic cross-sectional view of a portion of the DAQ module shown in FIG. 2 in accordance with aspects of the present subject matter.

Referring now to FIG. 3, a simplified, schematic cross-sectional view of a portion of the DAQ module 100 described above with reference to FIG. 2 is illustrated in accordance with aspects of the present subject matter, particularly illustrating the area within the module housing 102 in which the cameras 130, 132 and lighting devices 140 are positioned relative to the optical window 134. As shown in FIG. 3, in addition to the cameras 130, 132 and lighting devices 140, the DAQ module 100 may also include a heat exchange 172 positioned relative the optical window 134. In general, the heat exchange 172 may be configured to function as a heat dissipation means for the lighting devices 140 and/or the cameras 130, 132.

In several embodiments, the heat exchanger 172 may include a base plate 174 supported directly above the optical window 134 and a plurality of fins 175 extending outwardly from the base plate 174. The base plate 174 may generally be configured to be thermally coupled to the lighting devices 140 and/or the cameras 130, 132 to allow heat generated by such components to be transferred to the heat exchanger 172 (e.g., via conduction), which can then be subsequently dissipated into the air being circulated within the module housing 102 via convection. In this regard, the fins 175 may generally function to increase the rate at which heat is being transferred from the heat exchanger 172 via convection by increasing the overall surface area of the heat exchanger 172.

Additionally, in several embodiments, the optical window 134 (which forms a portion of the bottom wall 103 of the module housing 102) may be segmented into two or more optical window sections. For instance, as shown in FIG. 3, in one embodiment, the optical window 134 may include an imaging window section 134A associated with the cameras 130, 132 (e.g., a separate imaging window section for each camera 130, 132 or a common imaging window sections for both cameras 130, 132) that is segmented or otherwise separated from the remainder of the optical window 134 (e.g., a lighting window section 134B). For instance, as shown in the illustrated embodiment, the imaging window section 134A is separated from the lighting window section 134B by an optical divider or wall 137. Such segmentation of the optical window 134 may prevent light from the lighting devices 140 from being internally reflected within the window 134 and negatively impacting the images being obtained via the cameras 130, 132. For instance, the divider 137 may serves as an "optical break" between the imaging window section 134 and the lighting window section 134B, thereby preventing the transmission of reflected light from the lighting window section 134B to the imaging window section 134. Of course, it should be appreciated that, in other embodiments, the optical window 134 may be configured as a non-segmented or continuous window.

The simplified, schematic cross-sectional view of FIG. 3 also illustrates an exemplary configuration for the air knife 186 used to clean the external surface 135 of the optical window 134. As shown in FIG. 3, the air knife 186 is mounted within or through a portion of the bottom wall 103 of the module housing 102 such that the flow channel 187 of the air knife 186 defines a flow path for directing pressurized air from the interior of the module housing 102 across the external surface 135 of the optical window 134. Specifically, as shown, the air knife 186 allows an airflow (indicated by arrows 188) to be directed from the interior of the module housing 102, through the bottom wall 103 of the housing 102, and along the exterior of the optical window 134, thereby providing a means for cleaning the exterior surface 135 of the optical window 134. Additionally, as indicated above, an air flap 190 may be provided in operative association with the air knife 186 to selectively open/close the flow channel 187 defined by the air knife 186. For instance, when there is a positive air pressure within the module housing 102 (e.g., due to operation of the fan 184 (FIG. 2), the air flap 190 may be opened to allow air to be directed through the air knife 186.

Figure 4:
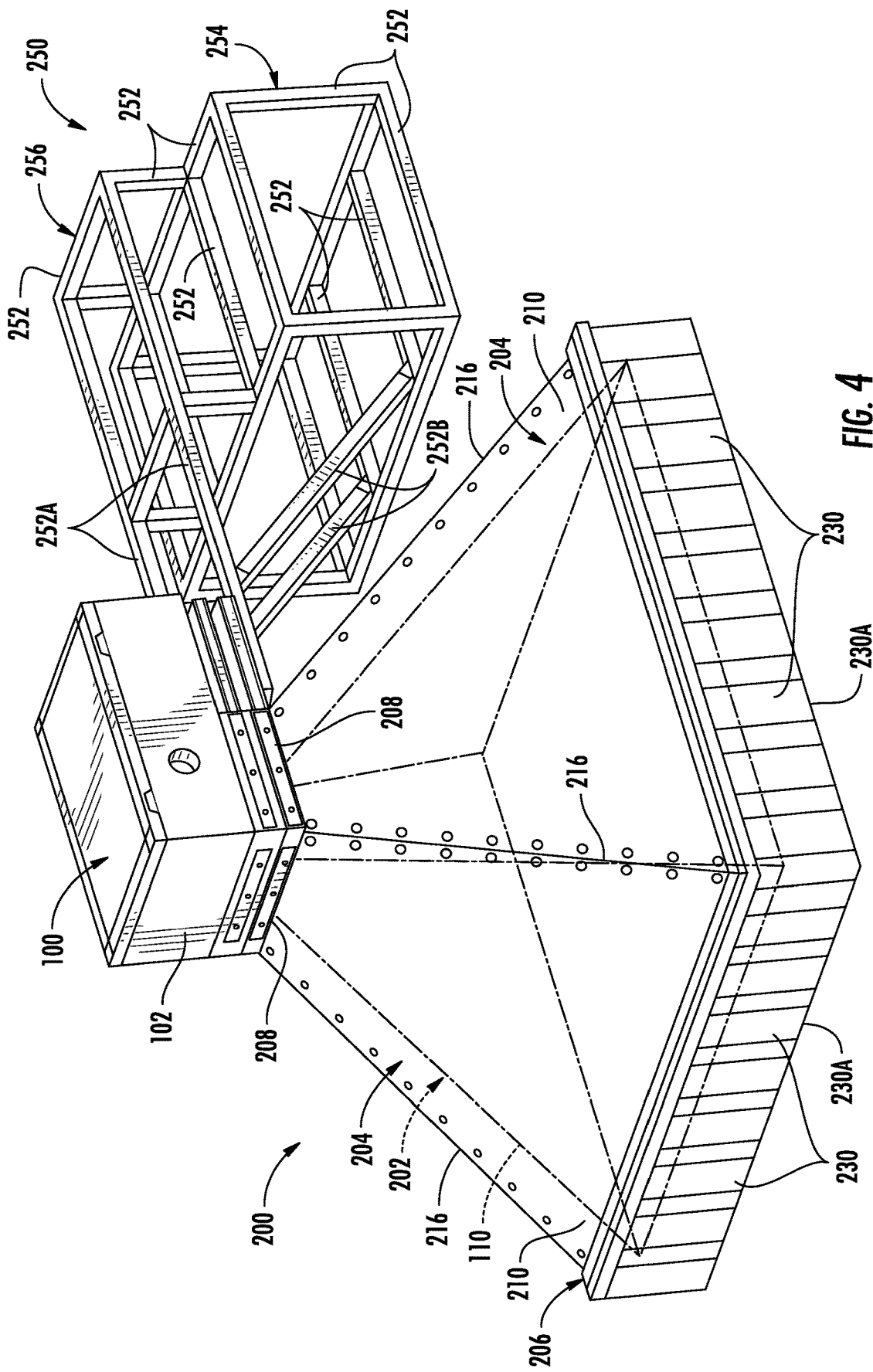
FIG. 4 illustrates a perspective view embodiments of a drape assembly and a frame assembly that may be utilized in connection with embodiments of the disclosed DAQ module in accordance with aspects of the present subject matter.
Figure 5:
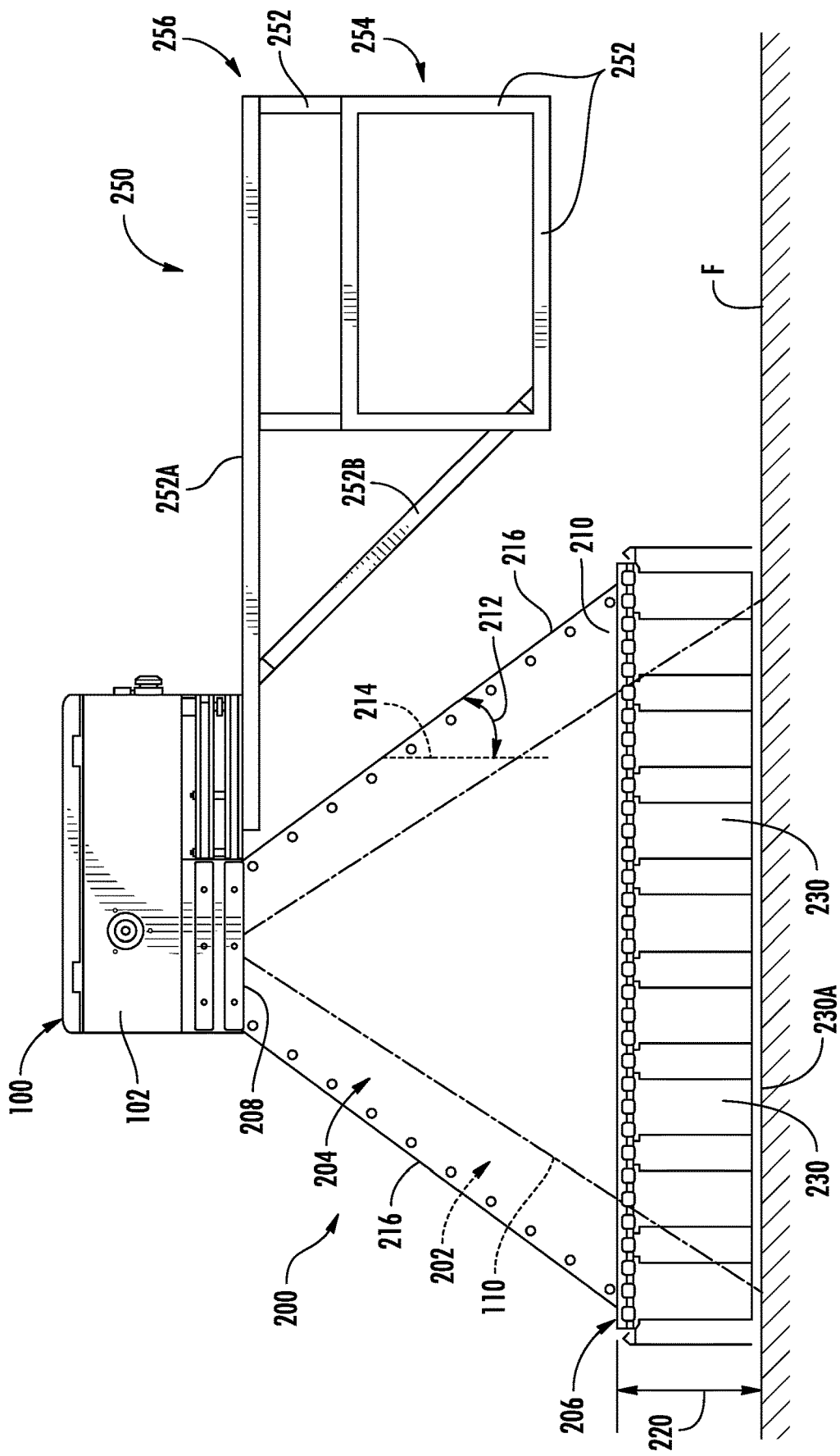
FIG. 5 illustrates a side view of the embodiments of the drape assembly and the frame assembly shown in FIG. 4.

Referring now to FIGS. 4 and 5, perspective and side views embodiments of a drape assembly 200 and frame assembly 250 that may be utilized in connection with embodiments of the disclosed DAQ module 100 are illustrated in accordance with aspects of the present subject matter. In several embodiments, the drape assembly 250 may be configured to be supported relative to the DAQ module 100 such that the assembly 250 at least partially shrouds an "imaging volume" 202 located directly below the DAQ module 100 that encompasses the field of view 110 of the imaging device(s) 108 of the DAQ module 100, thereby preventing or minimizing the amount of dust or debris that is directed across or through the field of view 110 of such imaging device(s) 108. Additionally, the illustrated frame assembly 250 may generally be configured to support the DAQ module 100 (and the drape assembly 200 suspended therefrom) relative to an associated agricultural machine (e.g., in a cantilevered arrangement).

As shown in FIGS. 4 and 5, the drape assembly 202 may include a plurality of flexible drape sections 204 (only two of which are visible in FIG. 4 and only one of which is visible in FIG. 5) supported relative to the DAQ module 100 and extending downwardly therefrom to a lower drape frame 206 of the drape assembly 204. For example, each flexible drape section 204 may extend vertically between a top end 208 and a bottom end 210, with the top end 208 of each drape section 204 being coupled to the DAQ module 100 (e.g., a portion of the module housing 102) and the bottom end 210 of each drape section 204 being coupled to the lower drape frame 206. In several embodiments, each drape section 204 may be oriented at a non-zero angle 212 (FIG. 5) relative to a vertical reference plane 214 (FIG. 5) between its top and bottom ends 208, 210 such that the drape sections 204 collectively define a diverging shape or profile as the drape sections 204 extend from the DAQ module 100 to the lower drape frame 206. Such a converging shape ensures that the imaging volume 204 being shrouded or encased via the drape sections 204 encompasses the field of view 100 of the imaging device(s) 108 as the field of view 110 expands or converges outwardly between the DAQ module 100 and the portions of the field (e.g., indicated by line F in FIG. 5) being imaged.

In general, the flexible drape sections 204 may be formed from any suitable material that allows the drape sections 204 to function as described herein, including the ability to flex or bow when the drape assembly 200 contacts an object (e.g., a rock) or other obstacle (e.g., a raised portion of the field F). For instance, in several embodiments, the drape sections 204 may be formed from polymer sheets or other flexible sheet-like materials. Additionally, it should be appreciated that, for lighting purposes, it is generally desirable that the drape sections 204 are transparent, thereby allowing ambient light to pass through the drape assembly 200 and illuminate the underlying portion of the field F. However, in other embodiments, the drape sections 204 may be semi-opaque or opaque, in which instance the lighting devices 140 of the DAQ module 100 may be configured to function as the primarily light source for illuminating the imaged portion of the field F.

Additionally, in several embodiments, adjacent drape sections 204 of the drape assembly 200 may be configured to move relative to each other, thereby allowing the drape sections 204 to accommodate instances in which a portion of the drape assembly 200 (e.g., the lower drape frame 206) contacts an obstacle/object within the field F. For instance, in one embodiment, each drape section 204 may extend freely between its top and bottom ends 208, 210 without being coupled to other adjacent drape sections 204 of the drape assembly 200, which may allow the drape section 204 to flex, bend, or otherwise move relative to the adjacent drape sections 204 if the horizontal orientation or vertical position of the lower drape frame 206 changes due to contact with an obstacle/object within the field F. In such an embodiment, the vertically extending edges 216 of adjacent drape sections 204 may, for example, be overlapped to prevent dust or other contaminates from passing between adjacent drape sections 204 and entering the otherwise enclosed imaging volume 202.

Moreover, in several embodiments, a length of each drape section 204 may generally be selected such that the lower drape frame 206 is suspended from the DAQ module 100 (i.e., via the drape sections 204) at a given height 220 (FIG. 5) above the surface of the field F, thereby providing some amount of vertical clearance between the lower drape frame 206 and the field F during normal operating conditions. For instance, in one embodiment, the height 220 may range from 1 about inch to about 12 inches, such as from about 1 inch to about 8 inches, or from about 2 inches to about 6 inches, and/or any other subranges therebetween.

Referring still to FIGS. 4 and 5, the lower drape frame 206 may generally correspond to any suitable frame or framelike component configured to define a closed-shape or perimeter having an enlarged cross-sectional area relative to the cross-sectional area of the closed-shape or perimeter of the enclosed space defined at the top ends 208 of the drape sections 204, thereby allowing each drape section 204 to be supported in its skewed or non-vertical orientation as it extends between the DAQ module 100 and the drape frame 206. In one embodiment, the drape frame 206 may correspond to a rigid or non-flexible frame that continuously maintains a fixed shape at the bottom ends 210 of the drape sections 204. For instance, the frame 206 may be formed from a plurality of rigid frame members (e.g., four frame members) coupled together to form the fixed shape of the frame 206 (e.g., a rectangular shape). Alternatively, the drape frame 206 may correspond to an elastic frame that can temporarily flex or bow when contracting an obstacle/object and then return to its desired shape. For instance, the drape frame 206 may be configured as a "hoop" frame formed by a ring-shaped or annular frame member. In such an embodiment, the annular frame member may, for example, be configured to temporarily flex or bow slightly before returning back to its original circular shape.

Additionally, in several embodiments, the drape assembly 200 may also include one or more drape flaps 230 suspended from the lower drape frame 206. For example, as shown in the illustrated embodiment, the drape assembly 200 includes a plurality of drape flaps 230 coupled to and extending downwardly from the drape frame 206 around its outer perimeter. In such an embodiment, the drape flaps 230 may be configured to at least partially span the height 220 or vertical clearance provided between the lower drape frame 206 and the surface of the field F. For instance, in one embodiment, the length of each drape flap 230 may be selected to be substantially equal to the desired vertical clearance between the lower drape frame 206 and the surface of the field (e.g., height 220) such that distal ends 230A of the flaps 230 are positioned directly above the surface of the field F or ride directly across the surface of the field F. Moreover, in one embodiment, each drape flap 230 may be configured to be pivotably coupled to the lower drape frame 206. Thus, when the drape flaps 230 contact an obstacle/object within the field F, the flaps 230 may pivot upwardly relative to the lower drape frame 206 to allow the flaps 230 to pass or ride over the obstacle/object.

Figure 6A:
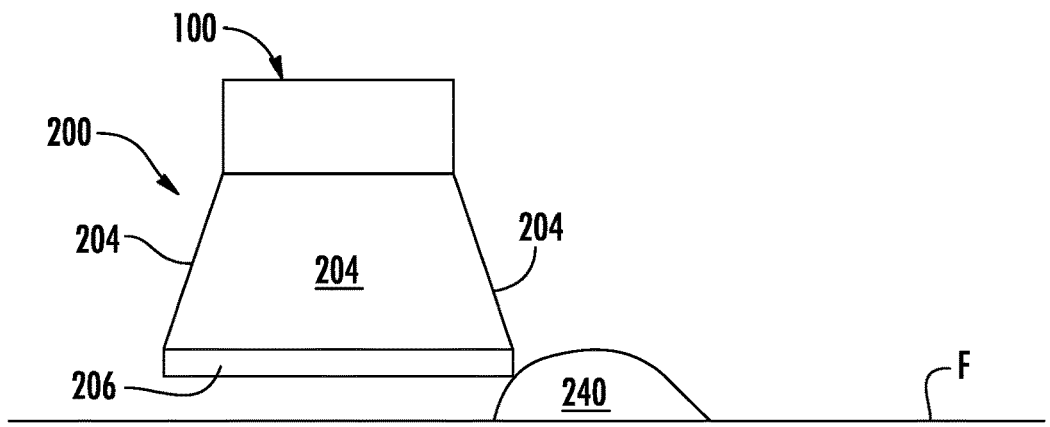
FIGS. 6A-6C illustrate a progressive series of side views of a simplified version of the drape assembly shown in FIGS. 4 and 5 as the drape assembly initially contacts an obstacle (e.g., rock) within the field (FIG. 6A), rides over the obstacle (FIG. 6B), and subsequently clears the obstacle (FIG. 6C) in accordance with aspects of the present subject matter.
Figure 6B:
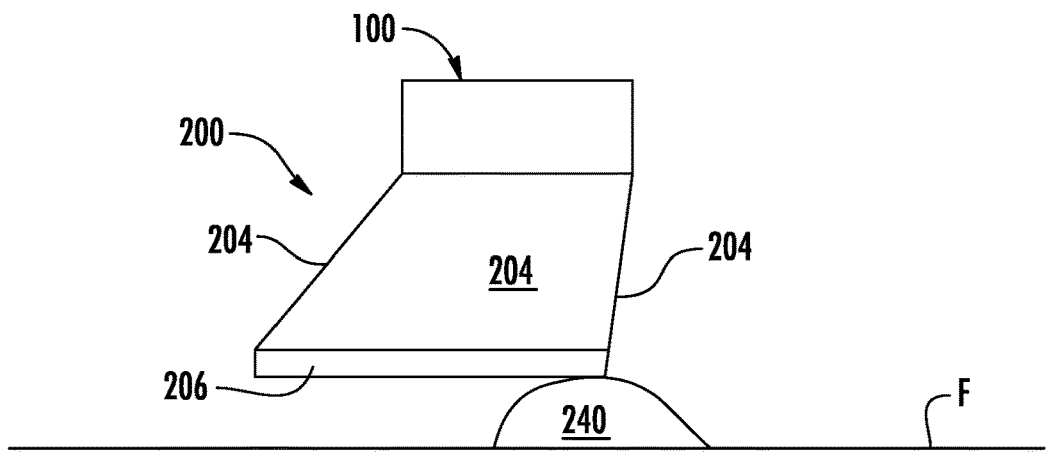
Figure 6C:
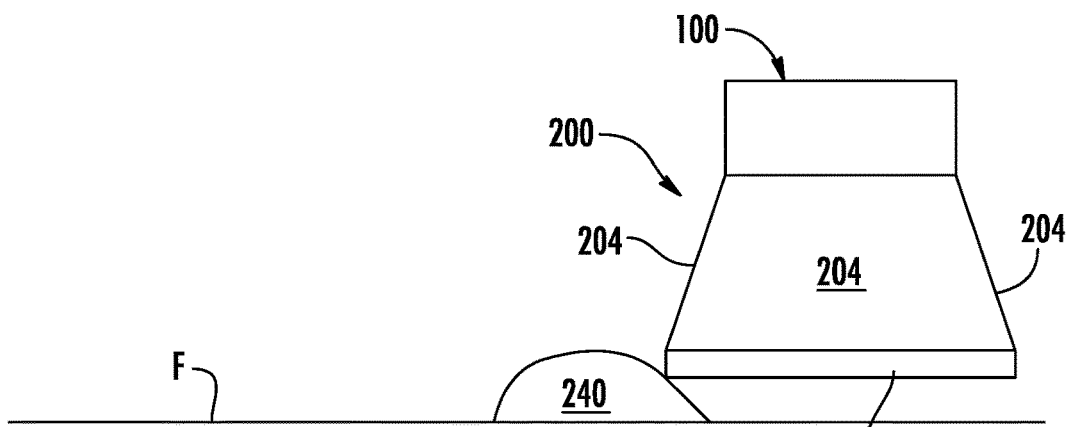

It should be appreciated that, by forming each drape section 204 from a flexible material (e.g., a transparent, flexible polymer sheet), the drape assembly 200 may generally be configured to swing or shift laterally when the lower drape frame 206 encounters an object/obstacle, thereby allowing the lower drape frame 206 to ride over and across such object/obstacle as the drape sections 204 flex or deform. For instance, FIGS. 6A-6C illustrate a progressive series of side views of a simplified version of the drape assembly 200 shown in FIGS. 4 and 5 as the drape assembly 200 initially contacts an obstacle (e.g., rock 240) within the field F (FIG. 6A), rides over the obstacle 240 (FIG. 6B), and subsequently clears the obstacle 240 (FIG. 6C). As shown, when the lower drape frame 206 initially contacts the obstacle 204, the drape sections 204 may bend or flex to allow the frame 206 to shift or move vertically upwardly as it rides over the obstacle 240. Once the obstacle is cleared, the weight of the drape frame 206 allows the drape assembly 200 to return to its original state.

Referring back to FIGS. 4 and 5, as indicated above, an example frame assembly 250 is illustrated in accordance with aspects of the present subject matter for supporting the DAQ module 100 (and the drape assembly 200 suspended therefrom) relative to an agricultural machine (e.g., the machine 10 shown in FIG. 1). As shown, the frame assembly 250 may generally include an assembly of frame members 252 configured to be coupled together to form a support structure for supporting the DAQ module 100 and drape assembly 200 in a cantilevered arrangement relative to an agricultural machine. In one embodiment, the various frame members 252 may be assembled such that the frame assembly 250 include a lower frame structure 254 (e.g., a box-like frame structure) and an upper frame structure 256 (e.g., a box like frame structure), with the lower frame structure 254 configured to be coupled to the agricultural machine (e.g., the forward end 38 of the work vehicle 12 shown in FIG. 1) and the upper frame structure 256 configured to be coupled to the DAQ module 100. For instance, as shown in FIGS. 4 and 5, the upper frame structure 256 may include a pair of elongated frame members 252A that extend outwardly relative to the lower frame structure 254 to allow the DAQ module 100 to be coupled thereto at a positioned spaced apart laterally from the lower frame structure 254, thereby providing the imaging device(s) 108 of the DAQ module 100 an unobstructed view to the surface of the underling field F. In such an embodiment, a pair of angled frame members 252B may be coupled between the lower frame structure 254 and the elongated frame members 252A to provide additional vertical support for supporting the DAQ module 100 and the drape assembly 200 in the cantilevered arrangement.

Additionally, in some embodiments, anti-vibration mounts may be provided between the DAQ module 100 and the frame assembly 250 to reduce the amount of vibrations transmitted from the agricultural machine 10 to the DAQ module 100. For instance, in one embodiment, coiled spring anti-vibration mounts may be coupled between the DAQ module 100 and the upper frame structure 256 (e.g., the elongated frame members 252A) to minimize the transmission of high frequency vibrations from the frame assembly 250 to the DAQ module 100. Alternatively, any other suitable vibration damping elements may be used as or in association with an anti-vibration amount to minimize vibration transmission and, thus, increase the performance and effectiveness of the DAQ module 100 in capturing field-related data (e.g., via the imaging devices 108).

It should be appreciated that the frame assembly 250 shown in FIGS. 4 and 5 is simply provided to illustrate one example of suitable mounting structure that may be used to support a DAQ module 100 (and, optionally, a drape assembly 200) relative to an agricultural machine. One of ordinary skill in the art will readily understand that various alternative arrangements, assemblies, structures, and/or the like may be used to support a DAQ module 100 (and, optionally, a drape assembly 200) relative to an agricultural machine in a manner that allow such module/assembly to function as described herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for acquiring data associated with an agricultural field, the system comprising:
an agricultural machine; and
a data acquisition (DAQ) module supported relative to the agricultural machine, the DAQ module comprising:
a module housing;
an optical window forming a portion of a wall of the module housing;
one or more sensing devices housed within the module housing, the one or more sensing device being configured to generate data associated with a condition of a field as the agricultural machine travels across the field, the one or more sensing devices being positioned within the module housing relative to the optical window such that a field of view of the one or more sensing devices is directed through the optical window; and
an air circulation system provided in operative association with the DAQ module, the air circulation system being configured to direct an airflow into an interior of the module housing for circulation therein to provide cooling for one or more components housed within the module housing, the air circulation system comprising an air knife configured to direct at least a portion of the airflow circulating within the interior of the module housing through the wall to an exterior of the module housing and then across an exterior surface of the optical window;
wherein the air circulation system further comprises an air flap provided in operative association with the air knife to allow a flow channel of the air knife to be selectively opened to permit the portion of the airflow to be directed from the interior to the exterior of the module housing and selectively closed to prevent the portion of the airflow from being directed from the interior to the exterior of the module housing; and
wherein the air circulation system further comprises a motor provided in operative association with the air flap, an operation of the motor being controlled to actuate the air flap in a manner that allows the flow channel of the air knife to be selectively opened and closed.

2. The system of claim 1, wherein the one or more sensing devices comprise one or more imaging devices configured to capture images of a portion of the field as the agricultural machine travels across the field.

3. The system of claim 2, further comprising one or more lighting devices positioned within the module housing relative to the optical window such that the one or more lighting devices are configured to direct light through the optical window to illuminate the portion of the field being imaged via the one or more imaging devices.

4. The system of claim 3, further comprising a heat exchanger thermally coupled to at least one of the one or more lighting devices or the one or more imaging devices such that heat generated by the at least one of the one or more lighting devices or the one or more imaging devices is transferred to the heat exchanger.

5. The system of claim 2, wherein the optical window is segmented such that at least a portion of the optical window aligned with the one or more imaging devices is optically isolated from another portion of the optical window.

6. The system of claim 2, wherein the agricultural machine comprises an agricultural work vehicle and the DAQ module is supported relative to the agricultural work vehicle in a cantilevered arrangement such that the one or more imaging devices have a field of view oriented generally perpendicular to a surface of the field.

7. The system of claim 2, further comprising a drape assembly suspended relative to the one or more imaging devices, the drape assembly being configured to at least partially shroud an imaging volume located underneath the DAQ module that encompasses a field of view of the one or more imaging devices.

8. The system of claim 7, wherein:
the drape assembly comprises a plurality of drape sections and a lower drape frame suspended relative to the DAQ module via the plurality of drape sections; and
each drape section of the plurality of drape sections includes a top end and a bottom end, with the top end of each drape section being coupled to the DAQ module and the lower end of each drape section being coupled to the lower drape frame.

9. The system of claim 8, wherein:
the plurality of drape sections comprises a plurality of flexible drape sections; and
each flexible drape section of the plurality of flexible drape sections is configured to flex with upward vertical movement of said lower drape frame.

10. The system of claim 1, wherein the air circulation system comprises:
an air intake conduit extending lengthwise between an intake end and an output end, with output end of the air intake conduit being provided in fluid communication with an intake port of the module housing; and
a fan housed within the module housing and being provided in fluid communication with the intake port of the module housing, the fan being configured to generate a suction force within the air intake conduit that results in the intake of air at the intake end of the intake conduit, with the generated airflow being directed through the air intake conduit for delivery to the module housing.

11. The system of claim 10, wherein:
the airflow generated by the fan creates a positive pressure within the interior of the module housing that exceeds an ambient pressure outside the module housing; and
the operation of the motor is controlled based on an operational state of the fan.

12. The system of claim 11, wherein the operation of the motor is controlled based on the operational state of the fan such that the flow channel of the air knife is closed when the fan is deactivated and opened when the fan is activated.

13. The system of claim 10, wherein:
the agricultural machine comprises an agricultural work vehicle and the DAQ module is supported relative to the agricultural work vehicle in a cantilevered arrangement; and
the air intake conduit extends from the DAQ module along a portion of the agricultural work vehicle such that the intake end of the air intake conduit is positioned proximal to an operator's cab of the agricultural work vehicle.

14. A system for acquiring data associated with an agricultural field, the system comprising:
an agricultural machine; and
a data acquisition (DAQ) module supported relative to the agricultural machine, the DAQ module comprising:
a module housing;
an optical window forming a portion of a bottom wall of the module housing;
one or more imaging devices configured to capture images of a portion of the field as the agricultural machine travels across the field, the one or more imaging devices being positioned within the module housing relative to the optical window such that a field of view of the one or more imaging devices is directed through the optical window; and a drape assembly suspended relative to the one or more imaging devices, the drape assembly being configured to at least partially shroud an imaging volume located underneath the DAQ module that encompasses the field of view of the one or more imaging devices;

wherein:

the drape assembly comprises a plurality of flexible drape sections and a lower drape frame suspended relative to the DAQ module via the plurality of flexible drape sections;

each flexible drape section of the plurality of flexible drape sections includes a top end and a bottom end, with the top end of each flexible drape section being coupled to the DAQ module and the lower end of each flexible drape section being coupled to the lower drape frame; and each flexible drape section of the plurality of flexible drape sections is configured to flex with upward vertical movement of said lower drape frame.

15. The system of claim 14, wherein:

the lower drape frame is configured to be suspended relative to the DAQ module via the plurality of flexible drape sections such that the lower drape frame is positioned a vertical distance from a surface of the field; and the drape assembly further comprises a plurality of drape flaps pivotably coupled to the lower drape frame, the plurality of drape flaps at least partially spanning the vertical distance defined between the lower drape frame and the surface of the field.

\* \* \* \* \*